US009132290B2

(12) United States Patent
Hodgson et al.

(10) Patent No.: US 9,132,290 B2
(45) Date of Patent: Sep. 15, 2015

(54) COSMETIC COMPOSITION

(75) Inventors: Erica Louise Hodgson, Ramsbury (GB); Teresa Barbara Crook, Camberly (GB); Naomi Mary Simpson, Twickenham (GB)

(73) Assignee: The Procter & Gamble Company, Cincinnati, OH (US)

( * ) Notice: Subject to any disclaimer, the term of this patent is extended or adjusted under 35 U.S.C. 154(b) by 63 days.

(21) Appl. No.: 13/186,539

(22) Filed: Jul. 20, 2011

(65) Prior Publication Data

US 2012/0021027 A1   Jan. 26, 2012

Related U.S. Application Data

(60) Provisional application No. 61/367,230, filed on Jul. 23, 2010.

(51) Int. Cl.
| *A61Q 1/00* | (2006.01) |
| *A61Q 17/04* | (2006.01) |
| *A61K 8/02* | (2006.01) |
| *A61K 8/06* | (2006.01) |
| *A61K 8/29* | (2006.01) |
| *A61K 8/49* | (2006.01) |
| *A61K 8/81* | (2006.01) |

(52) U.S. Cl.
CPC .............. *A61Q 17/04* (2013.01); *A61K 8/0204* (2013.01); *A61K 8/064* (2013.01); *A61K 8/29* (2013.01); *A61K 8/4946* (2013.01); *A61K 8/8176* (2013.01)

(58) Field of Classification Search
None
See application file for complete search history.

(56) References Cited

U.S. PATENT DOCUMENTS

| 2,831,854 | A | 4/1958 | Tucker et al. |
| 2,900,306 | A | 8/1959 | Slater |
| 3,255,082 | A | 6/1966 | Barton |
| 3,755,560 | A | 8/1973 | Dickert et al. |
| 3,963,699 | A | 6/1976 | Rizzi et al. |
| 4,005,195 | A | 1/1977 | Jandacek |
| 4,005,196 | A | 1/1977 | Jandacek et al. |
| 4,126,679 | A | 11/1978 | Davy et al. |
| 4,138,306 | A | 2/1979 | Niwa |
| 4,151,272 | A | 4/1979 | Geary et al. |
| 4,154,816 | A | 5/1979 | Roehl et al. |
| 4,168,128 | A | 9/1979 | Fillmore et al. |
| 4,202,879 | A | 5/1980 | Shelton |
| 4,226,889 | A | 10/1980 | Yuhas |
| 4,228,277 | A | 10/1980 | Landoll |
| 4,229,432 | A | 10/1980 | Geria |
| 4,268,499 | A | 5/1981 | Keil |
| 4,280,994 | A | 7/1981 | Turney |
| 4,322,400 | A | 3/1982 | Yuhas |
| 4,346,079 | A | 8/1982 | Roehl |
| 4,383,988 | A | 5/1983 | Teng et al. |
| 4,421,769 | A | 12/1983 | Dixon et al. |
| 4,517,360 | A | 5/1985 | Volpenhein |
| 4,518,772 | A | 5/1985 | Volpenhein |
| 4,725,432 | A | 2/1988 | May |
| 4,759,924 | A | 7/1988 | Luebbe et al. |
| 4,797,300 | A | 1/1989 | Jandacek et al. |
| 4,816,261 | A | 3/1989 | Luebbe et al. |
| 4,840,511 | A | 6/1989 | Fattori et al. |
| 5,011,681 | A | 4/1991 | Ciotti et al. |
| 5,017,398 | A | 5/1991 | Jandacek et al. |
| 5,019,375 | A | 5/1991 | Tanner et al. |
| 5,026,193 | A | 6/1991 | Lucas |
| 5,085,856 | A | 2/1992 | Dunphy et al. |
| 5,104,646 | A | 4/1992 | Bolich, Jr. et al. |
| RE33,996 | E | 7/1992 | Jandacek |
| 5,306,514 | A | 4/1994 | Letton et al. |
| 5,306,515 | A | 4/1994 | Letton et al. |
| 5,306,516 | A | 4/1994 | Letton et al. |
| RE34,617 | E | 5/1994 | Jandacek et al. |
| 5,688,831 | A | 11/1997 | El-Nokaly et al. |
| 5,750,096 | A | 5/1998 | Guskey |
| 5,939,082 | A | 8/1999 | Oblong et al. |
| 6,053,650 | A | 4/2000 | Bennett et al. |
| 6,060,547 | A | 5/2000 | Canter et al. |
| 6,126,352 | A | 10/2000 | Wiley |
| D626,852 | S | 11/2010 | Kruetzkamp et al. |
| D627,228 | S | 11/2010 | Kruetzkamp et al. |
| D627,663 | S | 11/2010 | Kruetzkamp et al. |
| D634,211 | S | 3/2011 | Kruetzkamp et al. |
| D634,212 | S | 3/2011 | Kruetzkamp et al. |

(Continued)

FOREIGN PATENT DOCUMENTS

| EP | 0024365 B1 | 11/1984 |
| EP | 0522624 A1 | 1/1993 |

(Continued)

OTHER PUBLICATIONS

CTFA International Cosmetic Ingredient Dictionary and Handbook, 3rd Ed., Cosmetic and Fragrance Assn., Inc., Washington, D.C. (1982) pp. 575-580.
CTFA International Cosmetic Ingredient Dictionary and Handbook, 7th Edition, vol. 2, pp. 1672, edited by Wenning and Mc Ewen (The Cosmetic, Toiletry, and Fragrance Association, Inc., Washington, D.C. 1997).
McCutcheon's Detergents and Emulsifiers, North American Edition, pp. 317-324 (1986).
"The Chemistry and Technology of Waxes", A. H. Warth, 2nd Edition, reprinted in 1960, Reinhold Publishing Corporation, pp. 391-393 and 421.

(Continued)

*Primary Examiner* — Jyothsna Venkat
(74) *Attorney, Agent, or Firm* — Betty J. Zea

(57) ABSTRACT

A film-forming cosmetic composition that provides superior feel, look, and wear characteristics while also delivering UV protection to the skin. The cosmetic composition may be in the form of a water-in-oil emulsion that includes a water compatible film-forming polymer, a sunscreen active, and one or more particles. The foundation provides suitable feel and appearance during application, UV protection, and excellent wear and appearance after application, yet provides flexible, light feel.

4 Claims, No Drawings

(56) References Cited

U.S. PATENT DOCUMENTS

| | | |
|---|---|---|
| 8,201,499 B2 | 6/2012 | Fujishiro |
| 2007/0071538 A1 | 3/2007 | Doria |
| 2009/0098170 A1 | 4/2009 | D'Acchioli et al. |
| 2010/0003205 A1 | 1/2010 | Elliott et al. |
| 2010/0003293 A1 | 1/2010 | Elliott et al. |
| 2010/0074928 A1 | 3/2010 | Elliott et al. |
| 2010/0166684 A1* | 7/2010 | Kokeguchi ............ 424/59 |
| 2011/0024719 A1 | 2/2011 | Sridhar et al. |
| 2011/0114257 A1 | 5/2011 | Kramer et al. |

FOREIGN PATENT DOCUMENTS

| | | |
|---|---|---|
| EP | 1870079 | * 12/2006 |
| JP | 61083110 | 4/1986 |
| JP | 07069636 | 3/1995 |

OTHER PUBLICATIONS

"The Petroleum Chemicals Industry", R. F. Goldstein and A. L. Waddeam, 3rd Edition (1967), E & F. N. Span Ltd., pp. 33-40.

"The Chemistry and Manufacture of Cosmetics", M. G. DeNavarre, 2nd edition (1970), Van Nostrand & Company, pp. 354-376.

Encylopedia of Chemical Technology:, vol. 24, Kirk-Othmer, 3rd Edition (1979) pp. 466-481.

International Search Report and Written Opinion of the International Searching Authority PCT/US2011/044627 dated Jul. 3, 2012, 15 pages.

* cited by examiner

COSMETIC COMPOSITION

CROSS REFERENCE TO RELATED APPLICATIONS

This application claims the benefit of U.S. Provisional Application No. 61/367,230, filed on Jul. 23, 2010.

FIELD OF THE INVENTION

The present invention relates to a cosmetic composition that contains a sunscreen active, a water compatible film forming polymer, and one or more particles. The cosmetic composition provides suitable feel and appearance during application, as well as excellent UV protection and wear and appearance benefits after application.

BACKGROUND OF THE INVENTION

One of the common uses of skin cosmetics is to improve the appearance of a person, especially the appearance of a person's face and/or skin. Typically foundations are used to enhance features, or mask perceived imperfections in them. As foundations are typically applied prior to other color cosmetics, they provide a uniform base of color and coverage which improve the overall appearance of make-up. Characteristics considered by consumers when choosing a foundation fall into three general areas; look (or appearance both upon application and after wear), feel (e.g., ease of application and the feel of the "made up" area), and wear (resistance to water, oil, abrasion, etc.). These foundations are generally available in the form of liquid, semi-liquid or cream suspensions, emulsions, gels, as well as pressed powders or anhydrous oil and wax compositions.

The skin cosmetic art has long sought to provide foundations that alter the appearance of the skin, especially the skin of the face. For example, foundations are used over the entire face to mask perceived imperfections in skin texture, pigmentation or vascularizaton. Unlike other color cosmetics, foundations are typically applied with the hand, and their presence is more visibly apparent than other skin cosmetics, such as moisturizers. Consumers desire a foundation that provides an even covering, without looking unnatural (e.g., "shiny" on the skin), and which can be applied easily with a pleasant feeling (e.g., is easy to spread over the skin but does not feel greasy). However, providing a foundation with all of these characteristics presents special challenges to the skilled artisan. In addition, foundations are typically used to cover relatively large areas of the skin. It is not uncommon for the skin of a person to have a non-uniform color or appearance, for example, due to the presence of a variety of known skin imperfections (e.g., hyper pigmentation). But conventional foundations generally uniform in color, and thus imperfections on a user's skin may be more apparent.

Typically, a consumer chooses foundations that provide a desired skin color. A variety of foundation colors can be provided by incorporating suitable pigment(s) in the foundation. Recently, increasing numbers of foundations incorporate UV benefit agents within the formula. However, the incorporation of UV benefit agents, due to the oily nature of the agent itself—or the chosen neutralizer in some cases, may result in the formation of a foundation film on skin that is not only greasy/oily to touch and shiny in appearance, but also a film that does not wear well on skin due to the increased mobility of the foundation film.

In an attempt to solve this problem, the art has sought new approaches that use oil soluble polymers at increased levels to help "fix" the film and mitigate the wear negatives. However, this approach itself brings negatives in terms of undesirable product feel. In addition, the incorporation of sunscreen actives can also make the film feel greasy and oily, thus amplifying the undesirable feel. While consumers may tolerate the undesirable feel in products where long wear is the primary concern, such products do not enjoy wide consumer acceptance in cosmetics.

Thus, there is a need to provide a film-forming cosmetic composition such as a foundation with UV benefits that also provides a desirable "feel" (e.g., it lacks greasiness, tackiness or stickiness; is smooth and dry; and exhibits suitable adherence to the skin). The film-forming foundation should also provides a "good look" (i.e., even coverage; blendable; and does not appear "heavy" when applied to the skin); should not be undesirably affected by skin secretions or water; and should not "bleed" with wear, does not crack, smudge, abrade, flake or peel.

Accordingly, it would be desirable to provide a film-forming skin cosmetic that provides a UV benefit, and is stable, easy and pleasant to apply, provides a good look, and also provides good wear characteristics.

SUMMARY OF THE INVENTION

In order to provide a solution to the problems above, disclosed herein is a non-tacky, film-forming cosmetic composition in the form of a water-in-oil emulsion. The cosmetic composition comprises a dispersed aqueous phase that includes from 0.5% to 10% of a water-dispersible or water-soluble, film-forming polymer that adheres to skin when applied to the skin. The aqueous phase also includes 0.1%-16% of a sunscreen active. The cosmetic composition further comprises one or more particles. The cosmetic composition also comprises a continuous oil phase that includes from 1% to 80% of an oil. The cosmetic composition exhibits substantially no perceived tackiness for up to two minutes after application to the skin UV protection, as well as excellent wear and appearance benefits after application.

DETAILED DESCRIPTION OF THE INVENTION

Because it can take up to 2 minutes for the average consumer to apply a foundation and because of the large surface area (typically >200 cm$^2$) of the face, it would be desirable to provide a foundation that can be easily blended, or even overcoated, after 2 minutes, without significant thickening or tacky feeling. The cosmetic compositions described herein may be formulated as a water-in-oil emulsion. The aqueous phase of the emulsion may include a film forming polymer, a plasticizing solvent, a UV protection agent, and optional water soluble additives. Water may be present at up to 60% by weight based on the weight of the cosmetic composition. In certain embodiments, water may be present in the cosmetic composition at between 10% and 50%. All amounts specified herein are by "weight percent" based on the weight of the cosmetic composition, unless otherwise specifically stated. Thus when specifying a non-solid ingredient, the amount is not in standard liquid measure.

"Foundation" means a liquid or semi-liquid skin cosmetic which includes, but is not limited to lotions, creams, gels, pastes, and the like. Typically, foundation is used to cover a large area of the skin, such as over the face, to provide a particular look. In a multi-step makeup regimen, foundation is typically the first cosmetic composition to be applied, followed by subsequent cosmetic compositions such as blush and eye shadow. A foundation may be an oil-in-water emulsion, water-in-oil emulsion formulation, or even a water-in-silicone emulsion formulation, where an "emulsion" is understood to describe the formulation of the foundation. It is well understood by those skilled in the art of cosmetic formulation that a water-in-oil emulsion has hydrophilic or aqueous material dispersed in hydrophobic or "oil"-like material. Thus the internal or dispersed phase is aqueous or "water"-like in nature and is called the "aqueous phase." The external or continuous phase is hydrophobic, and is called the "oil phase."

Film Forming Polymer

The present cosmetic composition may include a film forming polymer that is compatible with the aqueous phase of the emulsion. In certain embodiments, the film forming polymer and the plasticizing solvent discussed in more detail below may be incorporated in the internal phase of the water-in-oil emulsion. By incorporating the film forming polymer and the plasticizing solvent in the aqueous phase, the unpleasant tacky sensation characteristic of polymers on the user's hands and fingers during the cosmetic's application may be minimized. The film forming polymer can be water dispersible, or water soluble, but is not a cross-linked or a water-swellable polymer. Of course, it is desirable for the polymer to be capable of forming a thin elastomeric film that physically adheres or interacts with the skin. It may also be desirable to choose film-forming polymers that are not tacky.

The film forming polymer may be selected to provide a finished foundation that has a glass transition temperature (Tg) of about room temperature (i.e., between 18° C. and 24° C.) to about body temperature (i.e., between 35° C. and 38° C.). "Glass transition temperature" or "Tg" generally refers to the temperature where a polymer softens or transitions from brittle to plastic, in the absence of plasticizers. It is believed, without being limited by theory, that a cosmetic composition that has a suitable Tg exhibits desirable flexibility during application and wear (i.e., does not feel stiff or brittle). When the Tg is too high, the cosmetic composition may be hard to apply, and may flake. If the Tg is too low, the cosmetic composition will be less adhesive (and perhaps more cohesive) and will tend to "ball up" on application. Of course, the Tg of the polymer itself can vary. For example, it is expected that polymers with Tg of up to about 60° C. or higher are useful, provided the finished formulation has the proper Tg. For example polyvinylpyrrolidone is thought to have a Tg greater than 90° C., but may be suitable for use herein. Suitable film forming polymers may be thermoplastic, rather than thermosetting. Additionally, the polymer should be selected to provide an aqueous phase that is fluid enough to be handled and reasonably incorporated into the final emulsion composition as the dispersed or internal phase. Gelled and extremely viscous solutions can be used, but may impact ease of incorporation or final viscosity. Thus, it may be desirable to select thermoplastic polymers that can be added at levels to derive film forming and extended benefits, while maintaining workability of the final aqueous phase.

Examples of film-forming polymers that have suitable Tg, skin adhering properties and viscosity include, sulfopolyester resins such as AQ sulfopolyester resins (e.g., AQ29D, AQ35S, AQ38D, AQ38S, AQ48S, and AQ55S available from Eastman Chemicals); Vinex resins, such as Vinex 2034, Vinex 2144, and Vinex 2019 available from Air Products; water dispersible acrylic resins such as Dermacryl® resins available from Azko Nobel; polyquaterniums such as those available from Guangzhou Tinci Materials Technology Co., Ltd. and Nalco Company; polyurethanes (e.g., Baycusan® C1000 series from Bayer Materials Sciences Co), polyvinlypyrrolidones ("PVP"), including Luviskol® K17, K30 and K90 available from BASF; water soluble copolymers of PVP, including PVP/VA S-630 and W-735 and PVP/dimethylaminoethyl-methacrylate copolymers (e.g., Copolymer 845 and Copolymer 937 available from ISP). Particularly suitable polymers include AQ38S and PVP. The polymer may be present at levels of from 0.5% to 10% by weight based on the weight of the cosmetic composition, for example, from 1% to 8% by weight. In certain embodiments, PVP may be used as the film-forming polymer at levels of from 1% to 5% by weight based on the weight of the cosmetic composition may be sufficient. In certain embodiments, sulfopolyester AQ38S may be used as the film forming polymer at levels of between 2% and 8% by weight based on the weight of the cosmetic composition.

Plasticizing Solvent

Plasticizing solvents suitable for use herein are slow-evaporating, water-miscible or dispersible cosolvents that are 1) generally recognized as safe or 2) include slow evaporating glycols and glycol ethers, such as propylene glycol; butylene glycol; hexylene glycol; glycerine; dipropylene glycol; dipropylene glycol methyl ether (commonly known as DPM); propylene glycol phenyl ether; and polyethylene glycols (PEGs) such as PEG 4 and PEG 8. Other exemplary plasticizing solvents include propylene carbonate, dimethyl isosorbide, and mixtures thereof. A wide variety of plasticizing solvents are listed in the CTFA International Cosmetic Ingredient Dictionary and Handbook, 3rd Ed., Cosmetic and Fragrance Assn., Inc., Washington D.C. (1982) pp. 575-580. The plasticizing solvent may be present in amounts of from 0.5% to 30% or even 5% to 20%, and generally appear in a ratio of solvent to polymer of from 10:1 to 1:1 or even 8:1 to 2:1. The plasticizing solvent is chosen to provide for water co-solvency, suitable solubility regarding the polymer, low volatility, stability, and safety (i.e., lack of toxicity). Thus, the cosmetic composition herein employs safe solvents that provide little or no sensation of tackiness or cooling (usually due to evaporation) on the applied area.

The plasticizing solvent may be chosen such that the polymer and plasticizing solvent are formulated in the aqueous phase of the emulsion, which may help reduce any tacky sensation of polymer contacting the user's hands and fingers during application of the cosmetic composition. Because the solvent exhibits a slow evaporation rate and is present in the aqueous phase, it helps extend the workability of the foundation and delays any perceived onset of tackiness for up to two minutes.

Particles

The cosmetic composition herein may include one or more particles for modifying the application and appearance of the film formed by the film forming polymer. For example, particles may be included in the cosmetic composition to help minimize the undesirable tacky sensation of sunscreen actives and film forming polymers on a user's hands as well as helping to "mattify" the film and extend the wear of the cosmetic composition. In certain embodiments, at least some of the particles may be in the form of pigments present in the oil phase. Such particles may be added to provide even coverage during initial application of the foundation.

Particles may be added to extend the wear of the foundation film by absorbing components of sebum and sweat, thereby limiting the mobility of the foundation film across skin. The amount of particles present is important because too few particles may result in a cosmetic composition that exhibits an undesirable shine when applied to the skin. On the other hand, too many particles may cause the cosmetic composition to exhibit an undesirable chalky appearance when applied to the skin. In addition, it is believed without being limited by theory, that the type of particles present in the cosmetic composition is important for providing a desirable appearance on skin. For example, the present cosmetic composition may be configured as a 3 particle composition and include particles that are selected to maximize the matte look and wear benefits of the composition. A matte look may be thought of as being the opposite of a shiny look, which is generally undesirable for certain cosmetic compositions such as foundations and concealers. Matte look is typically generated when the surface topography of the foundation film is rough, thus increasing the amount of diffuse back-scatter of light from the surface of the foundation film. In certain embodiments, rough surface topography may be generated by using particles which fall within each of the 3 categories below, and it is most effective when each of these categories is represented.

Surface Topography Modifiers ("STMs") are particles that typically have minimal interaction with ingredients in the formula and exhibit relatively low oil absorption characteristics, which enables the STMs to be very efficient in a system where there is a high level of volatiles. However, in a composition where non-volatiles components are present, the inability of the STMs to absorb oil means that they tend to be "swamped" by the non-volatile components of the composition, and therefore do not generate a rough film surface topography. An exemplary STM is Aluminum Starch Octane Succinate having an average particle size of from 10 to 75 microns (e.g., 10-30 microns). While other particle sizes may be suitable for use, particle sizes above 75 microns may cause the cosmetic composition to have an undesirable gritty feel.

Locking Oil Absorbers ("LOAs") are particles that tend to absorb oil and lock it into the particle. With the oil absorbed from the film, these particles are able to at least partially stick out of the surface of the dry film, creating a rough surface topography and matte look. Nonlimiting examples of this type of particle are talc, isopropyl titanium triisostearate, and a microsphere complex based off ethylene/methacrylate copolymer. Suitable average particle sizes for LOAs are between 15-50 microns (e.g., 20-30 microns).

Releasing Oil Absorbers ("ROAs") are particles that absorb oil but are able to release it back into the film so that the film remains wetted That is, the ROAs are able to absorb oil from the cosmetic composition to help generate a rough surface topography, but are also able to release at least some of the oil back to the film to ensure that a chalky/dry look is not generated over time. An example of an ROA type of particle is a spherical silica particle such as Spheron P1500/L1500. Suitable average particle sizes for the ROAs are between 1 and 20 microns (e.g., between 2 and 15 microns, or about 5 microns).

It may be desirable to provide suitable particles at an amount of from 0.01% to 40%, from 0.1% to 30%, from 0.5% to 10%, or even 1-7.5% by weight, based on the weight of the cosmetic composition. Surprisingly, it has been found that by incorporating the particles in the composition at a particular ratio relative to one another, it is possible to provide a cosmetic composition with a desirable end look effect and that is not undesirably expensive to make. In certain embodiments, the particles may be included in the cosmetic composition at a wt % ratio range of STM:LOA:ROA of 25:25:1 to 15:5:1 by weight based on the weight of the composition. In certain embodiments, the particles may be included in the composition at wt % a ratio of 25:5:1 wherein the particle types are present at 2.5 wt %, 0.5 wt %, and 0.1 wt %, respectively. A particularly suitable example of the present cosmetic composition has the particles present in a wt % ratio of STM:LOA:ROA is 17:17:1, wherein the particle types are present at 2.6%, 2.6%, and 0.16%, respectively. It is to be appreciated that particle ratios that fall outside of this range may still be able to provide a suitable end look effect, for example, by using a disproportionately large amount of LOAs or even the LOAs alone. But LOAs are known to be more expensive than the other particle types, and it has been found that LOAs may undesirably impact the rheology of the composition by making it too thick for suitable application. Additionally, if the LOA is used alone, it may become more difficult or even impossible to minimize the chalky look of the film. Using STMs alone would not provide the desired end effect because STMs are generally not effective at absorbing oil, and therefore in a sunscreen system, for example, they would only be partially effective. In addition, excessive use of STM type particles may undesirably impact the rheology and/or feel of the composition in the same or similar was as the LOA type particles described above. Using ROAs alone would not provide the desired end effect unless they were also of large enough particle size to break through the surface of the film and create a rough surface topography in a system where the non-volatile sunscreen is present.

Other materials suitable for forming one or more of the particle types described herein include silicas, starch materials, ethylene methacrylate copolymers and mixtures of these. For example, spherical silica (Spheron P1500, Spheron L1500, Spheron LC-KAA, Spheron 20 MB) from Presperse Chemicals), hydrated silica, silicone treated silica beads, mica, talc, nylon 12 and nylon 6 (Orgasol series from Lipo Chemicals), polyethylene, aluminum starch octenyl succinate (Dry Flo, Dry Flo Plus from National Starch), methylsilsequioxane resin microspheres, (Tospearl 145A or Tospearl 2000 from Momentive Performance Materials); Micropearl M 100 (microspheres of polymethylmethacrylates) from Seppic; Trefil E 506C or Trefil E 505C (particles of crosslinked polydimethylsiloxanes) from Dow Corning Toray Silicone, Orgasol 2002D Nat $CO_5$ (particles of polyamide) from Atochem, Dynospheres (polystyerene microspheres) from Dyno Particles, FloBeads & microsphere complexes based off ethylene methacrylate copolymer (SPCAT12, SPCM12, DSPCS Series sold by Kobo Products), Microthene (polyethylene), Micropoly 220 (polyethylene), silica, or mixtures thereof. Styrene/DVB copolymers (Ganzpearl GS-0605 and GS-0805 from Presperse), PTFE (Microslip 519 from Presperse), PMMA (SUNPMMA-C000130 from Sunjin are also suitable.

Sunscreen Active

The present cosmetic composition may include a sunscreen active present within the external or internal phase of the emulsion. A sunscreen active is generally recognized as an ingredient or composition that absorbs or reflects at least some of the sun's ultraviolet (UV) radiation and is typically incorporated into a topical product for skin. When incorporated into the internal phase of the emulsion, the sunscreen active may help minimize the unpleasant tacky sensation of a sunscreen active on a user's hands and fingers during the application of the cosmetic composition. However, it does not minimize the impact on appearance of the film (undesirable shiny, greasy appearance) that these UV protection agents have.

Suitable sunscreen actives may be organic or inorganic. Organic sunscreen actives may be hydrophilic organic sunscreen actives, hydrophobic organic sunscreen actives, and mixtures thereof. A particularly suitable sunscreen active is a UV absorbing organic sunscreen active present at, for example, from 0.1% to 16%, from 0.2% to 12%, or even from 0.5% to 8% by weight based on the weight of the UV absorbing organic sunscreen composition. Exemplary sunscreen actives are described in the CTFA International Cosmetic Ingredient Dictionary and Handbook, 7$^{th}$ edition volume 2, pp. 1672, edited by Wenning and Mc Ewen (The Cosmetic, Toiletry, and Fragrance Association, Inc., Washington, D.C. 1997).

Suitable examples of inorganic sunscreen actives include, without limitation, titanium dioxide and zinc oxide particles. Such metal oxide particles may have an average primary particle size equal to or less than 100 nm. These particles may be selected from sunscreen grade titanium dioxide, sunscreen grade zinc oxide and mixtures thereof. These particles may be surface-treated and/or coated, using conventional treatments. Examples of commercially available sunscreen metal oxide particles include M262 from Kemira Corp., TTO S-3 and TTO S-4 from Ishihara Corp. The composition may include from 0.05% to 15%; 0.5% to 10%; or even from 1% to 5% of sunscreen grade metal oxide particles by weight of the total composition.

Suitable examples of hydrophobic organic sunscreen actives include, without limitation, cinnamate derivatives (e.g., ethylhexyl methoxycinnamate and ethyl methoxycinnamate); alkyl β,β-diphenylacrylate derivatives (e.g., ethyl 2-cyano-3,3-diphenylacrylate) and 2-ethylhexyl 2-cyano-3,3-diphenylacrylate); α-cyano β,β-diphenylacrylate derivatives; anthranilate derivatives (e.g., methyl anthranilate); benzophenone derivatives (e.g., methyl benzophenone and trimethylbenzophenone); camphor derivatives (e.g., benzylidene camphor sulfonic acid); dibenzoylmethane derivatives (e.g., butyl methoxydibenzoylmethane, ethylhexyl methoxydibenzoylmethane, and isopropyl dibenzoylmethane); p-aminobenzoic derivatives (e.g., p-aminobenzoic acid butyl ester and p-aminobenzoic acid); salicylic derivatives, triazine derivatives (tris-biphenyl triazine); and mixtures thereof. Particularly suitable hydrophobic organic sunscreen actives are selected from 2-ethylhexyl-p-methoxycinnamate, 4-(1,1-dimethylethyl)-4'-methoxydibenzoylmethane; 4-isopropyldibenzoylmethane; 4-(1,1-dimethylethyl)-4'-methoxydibenzoylmethane, 2-ethylhexyl-2-cyano-3,3-diphenylacrylate, or mixture thereof. 4-(1,1-dimethylethyl)-4'-methoxydibenzoylmethane, also known as butyl methoxydibenzoylmethane or Avobenzone, is commercially available Parsol™ 1789 from Givaudan Roure S. A. and Eusolex™ 9020 from Merck & Co., Inc. 4-isopropyldibenzoylmethane, also known as isopropyldibenzoylmethane, is commercially available as Eusolex™ 8020 from Merck & Co., Inc. 2-ethylhexyl-2-cyano-3,3-diphenylacrylate, also known as Octocrylene, is commercially available as Uvinul N539 SG from BASF; and Eusolex OCR from Rona/Merck. Examples of commercially available 2-ethylhexyl-p-methoxycinnamate, also known as Octyl Methoxy Cinnamate, include Uvinul MC80 from BASF and Neo Heliopan AV from Symrise.

A suitable example of a hydrophilic organic sunscreen active is 2-phenylbenzimidaole-5-sulfonic acid, also known as PBSA. 2-phenylbenzimidaole-5-sulfonic acid is commercially available under the product name Eusolex 232 from Rona/Merck. The composition may include from 0.1% to 16%, from 0.2% to 12%, from 0.5% to 10%, or even 0.5% to 7% of at least one organic sunscreen active by weight of the total composition.

Oil

The cosmetic composition herein may further comprise one or more oils that act as a "carrier solvent" for the other formula components and allow for the formula to be spread around the face in a suitable manner. This oil may be selected from volatile oils, non-volatile oils or mixtures thereof. As used herein, the term "non-volatile" when employed in relation to an oil includes oils that fulfill at least one of the following definitions: (a) the oil exhibits a vapor pressure of no more than 0.2 mm Hg at 25° C. and one atmosphere pressure; or (b) the oil has a boiling point at one atmosphere of at least 300° C. The present cosmetic composition may include from 1% to 80%, from 10% to 70%, or even from 15% to 65%, of an oil by weight based on the cosmetic composition. Optionally, the cosmetic composition may include from 0.1% to 20% or from 1 to 10% by weight of a non-volatile oil based on the weight of the cosmetic composition. The oil may include volatile, non-polar oils; non-volatile, relatively polar oils; non-volatile, non-polar oils; and/or non-volatile paraffinic hydrocarbon oils; each discussed more fully hereinbelow. The phrase "relatively polar" means more polar than another material in terms of solubility parameter; i.e., the higher the solubility parameter the more polar the liquid. The term "non-polar" means that the material has a solubility parameter below about 6.5 (cal/cm$^3$)$^{0.5}$. The oils may be selected to have a particular viscosity, depending on the desired use.

Non-Polar, Volatile Oils

Non-polar, volatile oil may be included in the cosmetic composition to impart desirable aesthetic properties (e.g., good spreadability, non-greasy and/or tacky feel, quick drying to allow pigment particles to set on skin) to the present cosmetic composition. Non-polar, volatile oils suitable for use herein include silicone oils; hydrocarbons; and mixtures thereof. The non-polar, volatile oils may be either saturated or unsaturated, have an aliphatic character and be straight or branched chains or even contain alicyclic or aromatic rings. Examples of suitable non-polar, volatile hydrocarbons for use herein include polydecanes such as isododecane and isodecane (e.g., Permethyl-99A which is available from Presperse Inc.), dodecanes and tetra dodecanes (such as Parafol 12-97 and Parafol 14 from Sasol), and the C7-C8 through C12-C15 isoparaffins (such as the Isopar Series available from Exxon Chemicals). Exemplary non-polar, volatile liquid silicone oils are disclosed in U.S. Pat. No. 4,781,917 issued to Luebbe et al. on Nov. 1, 1988. Additionally, a description of various volatile silicone oils may be found in Todd et al., "Volatile Silicone Fluids for Cosmetics", Cosmetics and Toiletries, 91:27-32 (1976). Particularly suitable volatile silicone oils include cyclic volatile silicones corresponding to the formula:

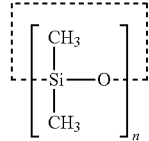

wherein n is from about 3 to about 7; and linear volatile silicones corresponding to the formula:

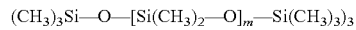

wherein m is from about 1 to about 7. Linear volatile silicone oils generally have a viscosity of less than about 5 centistokes at 25° C., whereas the cyclic silicones have viscosities of less than about 10 centistokes at 25° C. Examples of suitable volatile silicone oils include cyclomethicones of varying viscosities, e.g., Dow Corning 200, Dow Corning 245, available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.). In addition, Caprylyl Methicone such as DC FZ3196 can be used. Other examples of non-polar, volatile oils are disclosed, for example, in Cosmetics, Science, and Technology, Vol. 1, 27-104 edited by Balsam and Sagarin, 1972.

Relatively Polar, Non-Volatile Oils

Non-volatile oil suitable for use with the present cosmetic composition may be "relatively polar" as compared to the non-polar, volatile oil discussed above. Therefore, the non-volatile co-solvent is more polar (i.e., has a higher solubility parameter) than at least one of the non-polar, volatile oils. Relatively polar, non-volatile oils potentially useful herein are disclosed, for example, in Cosmetics, Science, and Technology, Vol. 1, 27-104 edited by Balsam and Sagarin, 1972; U.S. Pat. No. 4,202,879 issued to Shelton on May 13, 1980; and U.S. Pat. No. 4,816,261, issued to Luebbe et al. on Mar. 28, 1989. Relatively polar, non-volatile oils suitable for use herein include silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile oils may be saturated or unsaturated, linear or branched, aromatic or aliphatic, and/or contain one or more ring structures. For example, fatty alcohols having from about 12-26 carbon atoms; fatty acids having from about 12-26 carbon atoms; esters of monobasic carboxylic acids and alcohols having from about 14-30 carbon atoms; esters of dibasic carboxylic acids and alcohols having from about 10-30 carbon atoms; esters of polyhydric alcohols and carboxylic acids having from about 5-26 carbon atoms; ethoxylated, propoxylated, and mixtures of ethoxylated and propoxylated ethers of fatty alcohols with from about 12-26 carbon atoms and a degree of ethoxylation and propoxylation of below about 50; and mixtures thereof are suitable. Other suitable examples include propoxylated ethers of C14-C18 fatty alcohols having a degree of propoxylation below about 50; esters of C2-C8 alcohols and C12-C26 carboxylic acids (e.g. ethyl myristate, isopropyl palmitate); esters of C12-C26 alcohols and benzoic acid (e.g. Finsolv TN supplied by Finetex); diesters of $C_2$-$C_8$ alcohols and adipic, sebacic, and phthalic acids (e.g., diisopropyl sebacate, diisopropyl adipate, di-n-butyl phthalate); polyhydric alcohol esters of C6-C26 carboxylic acids (e.g., propylene glycol dicaprate/dicaprylate, propylene glycol isostearate); and mixtures thereof; branched-chain aliphatic fatty alcohols having from about 12-26 carbon atoms; isocetyl alcohol; octyldecanol; octyldodecanol; and undecylpentadecanol; and octyldodecanol. Aliphatic fatty alcohols such as those disclosed herein may be particularly useful in combination with the volatile liquid silicone oils discussed herein to adjust the average solubility of the solvent. In addition, materials such as Diethylhexyl carbonate (such as Tegosoft DEC from Evonik) can be used.

Non-Polar, Non-Volatile Oils

In addition to the liquids discussed above, the solvent may optionally include non-volatile, non-polar oils. Examples of non-volatile, non-polar emollients are disclosed, for example, in Cosmetics, Science, and Technology, Vol. 1, 27-104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. The non-volatile oils suitable for use herein include non-volatile polysiloxanes, paraffinic hydrocarbon oils, and mixtures thereof. Suitable examples of polysiloxanes include, without limitation, polyalkylsiloxanes, polyarylsiloxanes, polyalkylarylsiloxanes, poly-ethersiloxane copolymers, and mixtures thereof.

Examples of non-volatile silicone emollients useful in the present cosmetic compositions include polydimethyl siloxanes having viscosities of from 1 to 100,000 centistokes at 25° C., for example, 2 to 400 centistokes at 25° C. Such polyalkylsiloxanes include the Viscasil® series (sold by General Electric Company) and the Dow Corning 200 series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid (sold by General Electric Company) and 556 Cosmetic Grade Fluid (sold by Dow Corning Corp.). Useful polyethersiloxane copolymers include, for example, a polyoxyalkylene ether copolymer having a viscosity of about 1200 to 1500 centistokes at 25° C. Such a fluid is available as SF1066 organosilicone surfactant (sold by General Electric Company). Polysiloxane ethylene glycol ether copolymers are preferred copolymers for use in the present compositions.

Examples of non-volatile paraffinic hydrocarbon oils include mineral oils and certain branched-chain hydrocarbons, such as those disclosed in U.S. Pat. No. 5,019,375 issued to Tanner et al. on May 28, 1991. Particularly suitable branched-chain hydrocarbons include Permethyl 103 A, which contains an average of about 24 carbon atoms; Permethyl 104A, which contains an average of about 68 carbon atoms; Permethyl 102A, which contains an average of about 20 carbon atoms; all of which may be purchased from Permethyl Corporation; and Ethylflo 364 which contains a mixture of 30 carbon atoms and 40 carbon atoms and may be purchased from Ethyl Corp. When used herein, volatile or non-volatile hydrocarbon oils may be present at concentrations less than 30%, from 1% to 25%, or even from 1% to 15%. Additional solvents useful herein are described in U.S. Pat. No. 5,750,096 to Gerald J. Guskey et al., issued May 12, 1998.

Emulsifier

Emulsifiers or surfactants can also be used herein to provide emulsion stability. It may be desirable to select emulsifiers that provide minimal no negative skin feel (e.g., greasiness, tackiness, poor spreadability). These emulsifiers may be nonionic, anionic or cationic. The present cosmetic composition may include from 0.01% to 10%, from 0.1% to 10%, or even from 0.1% to 5% of emulsifiers by weight, based on the weight of the cosmetic composition. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986). Illustrative nonionic surfactants are alkoxylated compounds based on C10-C22 fatty alcohols and acids, and sorbitan. These materials are available, for instance, from the Shell Chemical Company under the Neodol trademark, Copolymers of polyoxypropylene-polyoxyethylene, sold by the BASF Corporation under the Pluronic trademark, are sometimes also useful. Alkyl polyglycosides available from the Henkel Corporation may also be utilized herein. Anionic type emulsifiers or surfactants include fatty acid soaps, sodium lauryl sulphate, sodium lauryl ether sulphate, alkyl benzene sulphonate, mono- and di-alkyl acid phosphates and sodium fatty acyl isethionate. Amphoteric emulsifiers or surfactants include such materials as dialkylamine oxide and various types of betaines (such as cocamidopiopyl betaine). Other examples of suitable emulsifiers can be found in U.S. Pat. No. 5,085,856 to Dunphy et al.; Japanese Patent Publication Sho 61-83110; European Patent Application EP 522624 to Dunphy et al.; U.S. Pat. No. 5,688,831 to El- Nokaly et al.; and Examples of suitable moistures can be found in Cosmetic Bench Reference, pp. 1.22, 1.24-1.26 (1996).

When the cosmetically acceptable carrier is a water-in-silicone emulsion, emulsifiers may be selected from polyoxyalkylene copolymers, polyglyceryl copolymers or mixtures thereof. Polyoxyalkylene copolymers, also known as silicone polyethers, are described in detail in U.S. Pat. No. 4,268,499. Examples of commercially available polyoxyalkylene copolymers include DC5225C or DC2-5185C (PEG/PPG-18/18 dimethicone available as blend with cyclopentasiloxane) from Dow Corning Corp.; and, KF6017, KF6028 (PEG-9 dimethicone) or KF6038 from Shin-Etsu Inc. Examples of commercially available polyglyceryl emulsifiers include KF6100 and KF6104 from Shin-Etsu Inc.

Elastomer

Elastomers may be used to modify the skin feel of the present cosmetic composition as well as the optical properties of the composition. In certain embodiments, the elastomer may include a cross-linked organopolysiloxane elastomer. The cross-linked organopolysiloxane elastomer is selected from emulsifying cross-linked organopolysiloxane elastomer, non-emulsifying cross-linked organopolysiloxane elastomer or mixtures thereof. As used herein, the term "non-emulsifying" when employed in relation to the cross-linked organopolysiloxane elastomer includes cross-linked organopolysiloxane elastomer comprising no polyoxyalkylene or polyglyceryl unit. As used herein, the term "emulsifying" when employed in relation to the cross-linked organopolysiloxane elastomer includes cross-linked organopolysiloxane elastomer comprising at least one polyoxyalkylene (e.g., polyoxyethylene or polyoxypropylene) or polygyceryl unit.

The present cosmetic compositions may contain from 0.01% to 15%, from 1% to 12.5%, or even from 2% to 10% by weight of a cross-linked organopolysiloxane elastomer based on the weight of the cosmetic composition. The composition may optionally include from 0.01% to 15% or even from 0.01% to 1% by weight of an emulsifying cross-linked organopolysiloxane elastomer based on the weight of the cosmetic composition and/or from 0.01% to 15% or even from 2% to 10% by weight of a non-emulsifying cross-linked organopolysiloxane elastomer based on the weight of the total composition. Examples of suitable starting material for the cross-linked organopolysiloxane elastomer include addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane; condensation-curing organopolysiloxane compositions which cure in the presence of an organotin compound or a titanate ester, by a condensation reaction between an hydroxyl-terminated diorganopolysiloxane and a hydrolyzable organosilane; peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Suitable non-emulsifying cross-linked organopolysiloxane elastomers are dimethicone/vinyl dimethicone crosspolymers. Examples of commercially available dimethicone/vinyl dimethicone crosspolymers include DC 9040, DC 9045 and DC 9041 from Dow Corning Corporation; SFE 839 from General Electric; KSG-15, KSG-16 and KSG-18 from Shin Etsu Chemical Company Ltd; and Gransil™ line of materials from Grant Industries. Examples of commercially available lauryl dimethicone/vinyl dimethicone crosspolymers include KSG-31, KSG-32, KSG-41, KSG-42, KSG-43, and KSG-44 from Shin Etsu Chemical Company Ltd.

Suitable examples of emulsifying cross-linked organopolysiloxane elastomers include polyoxyalkylene-modified elastomers formed from divinyl compounds, particularly siloxane polymers with at least two free vinyl groups, reacting with Si—H linkages on a polysiloxane backbone. Examples of commercially available emulsifying cross-linked organopolysiloxane elastomers include KSG-21 and KSG-210 and KSG-320 from the Shin-Etsu Chemical Company Ltd. Examples of commercially available emulsifying cross-linked organopolysiloxane elastomers comprising polyglyceryl units include KSG 710 and KSG-800 from the Shin-Etsu Chemical Company Ltd.

Metal Oxides

The present cosmetic composition may also include from 0.05% to 15%, 0.1% to 12%, or even from 0.5% to 10% of pigmentary metal oxide particles such as pigmentary grade iron oxide particles and pigmentary grade titanium dioxide particles to provide coverage and colour to the skin Pigmentary iron oxide particles may have an average primary particle size greater than 100 nm or greater than 100 nm to 500 nm and include pigmentary yellow iron oxide particles, pigmentary red iron oxide particles, pigmentary black iron oxide particles and mixture thereof. Pigmentary yellow iron oxide is also known as goethite, ferric oxide hydrate or CI 77492. Pigmentary red iron oxide is also known as haematite, ferric oxide and CI 77491. Pigmentary black iron oxide is known as magnetite, ferrous-ferric oxide and CI 77499. The pigmentary metal oxide particles may be surface-treated and/or coated, using conventional treatments. Commercially available pigmentary iron oxide particles include Cosmetic Red Iron Oxide C7054, Cosmetic Yellow Iron Oxide C7055, Unipure Black LC989 AS-EM from LCW-Sensient Cosmetic Technologies.

The present cosmetic composition may contain from 0.05% to 20%, from 1% to 15%, from 2% to 12.5%, or even from 3% to 10% of iron containing titanium dioxide particles to reduce blue reflectance from skin, for example, as taught in copending US. Publication Nos. 2010-0074928 A1, US 2010-0003205 A1, and US 2010-0003293 A1. Suitable raw materials for such particles are manufactured by Ishihara Sangyo Kaisha Ltd under the trade name FX50. This raw material comprises iron-containing titanium dioxide particles surface treated with aluminium hydroxide present as aluminium oxide $Al_2O_3$, and optionally, being coated hydrophobically with dimethicone and methicone. This raw material may be from 86% to 92% titanium dioxide by weight of the total particle, 1% to 3% $Al_2O_3$ by weight of the total particle, 5% to 10% iron by weight of titanium dioxide, and have an average surface area from 10 $m^2/g$ to 15 $m^2/g$ and an average primary particle size from 150 nm to 190 nm. This raw material may be manufactured according to the process detailed in the Japanese patent application H5-231041, filed on 24 Aug. 1993. Alternative suitable raw materials are manufactured by Nikko Rica Corporation under the trade name Fincera®.

The present cosmetic composition may also contain iron oxide particles having an average surface area from 30 $m^2/g$ to 150 $m^2/g$, preferably from 50 $m^2/g$ to 150 $m^2/g$, more preferably from 60 $m^2/g$ to 150 $m^2/g$. Such particles are transparent particles being conventionally used in cosmetic compositions, and are not considered pigmentary grade particles. The iron oxide particles may have an average primary particle size of less than or equal to 100 nm as measured by transmission electron microscopy. These iron oxide particles may be selected from transparent yellow iron oxide particles, transparent red iron oxide particles, transparent black iron oxide particles, and mixture thereof. Transparent yellow iron oxide is also known as goethite, ferric oxide hydrate or CI 77492. Transparent red iron oxide is also known as haematite, ferric oxide and CI 77491. Transparent black iron oxide is known as magnetite, ferrous-ferric oxide and CI 77499. Examples of commercially available transparent iron oxide particles include FAF40TRR, FAF40TRY, CM3F30TRR, CM3F40TRR, CM3F30TRY and CM3F40TRY supplied by Kobo; Trionix® materials from Noviant; and, the SunChroma® materials from Sun Chemicals.

The cosmetic composition may comprise from 0.05% to 10%, from 0.1% to 5%, or even from 0.1% to 4%, iron oxide particles having an average surface area from 30 $m^2/g$ to 150 $m^2/g$ by weight of the total composition.

Fragrance

In addition, the composition may comprise fragrance. Whilst not wishing to be bound by theory, it is believed that extending the life of the fragrance by using a fragrance technology helps reinforce the long wear benefits of the foundation. Suitable fragrance technologies include cyclodextrins (beta, gamma, alpha and derivatives), plus those whereby the fragrance is entrapped within solid entrapping particles as described in US20090098170 A1.

Optional Ingredients

Skin Conditioning Agent

Optionally, the present cosmetic compositions may contain a skin conditioning agent. These agents may be selected from exfoliants or emollients. Exfoliants may be selected from C2-C30 alpha-hydroxycarboxylic acids, beta-hydroxycarboxylic acids and salts of these acids. Most preferred are glycolic, lactic and salicylic acids and their ammonium salts. Amounts of the exfoliants may range from 1 to 15%, preferably from 2 to 10% by weight. A wide variety of C2-C30 alpha-hydroxycarboxylic acids may be employed. Suitable examples of which include: alpha-hydroxyethanoic acid, alpha-hydroxypropanoic acid, alpha-hydroxyhexanoic acid, alpha-hydroxyoctanoic acid, alpha-hydroxydecanoic acid, alpha-hydroxydodecanoic acid, alpha-hydroxytetradecanoic acid, alpha-hydroxyhexadecanoic acid, alpha-hydroxyoctadecanoic acid, alpha-hydroxyeicosanoic acid, alpha-hydroxydocosanoic acid, alpha-hydroxyhexacosanoic acid, and alpha-hydroxyoctacosanoic acid.

When the conditioning agent is an emollient, it may be selected from hydrocarbons, fatty acids, fatty alcohols and esters. Isononyl isononanoate is a particularly suitable emollient conditioning agent. Other hydrocarbons that may be employed include mineral oil, polyolefins such as polydecene, and paraffins such as isohexadecane (e.g. Permethyl 99 Registered TM and Permethyl 101 Registered TM). The present cosmetic compositions are substantially free of semisolid hydrocarbons such as petrolatum, lanolin and lanolin derivatives, sterols (e.g., ethoxylated soya sterols), high molecular weight polybutenes and coco butter. By "substantially free," as used herein, means that the concentration of the semi-solid hydrocarbons are less than 10%, less than 5%, less than 2%, or even 0. Without being limited by theory, such semi-solid hydrocarbons tend to mask the sensory benefits of the siloxane elastomer compositions such as the non-greasy, light feel of the present invention.

Fatty acids and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids and alcohols.

Oily ester emollients may be those selected from one or more of the following classes: 1) Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil; 2) Acetoglyceride esters, such as acetylated monoglycerides; 3) Ethoxylated glycerides, such as ethoxylated glyceryl monostearate; 4) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate; 5) Alkenyl esters of fatty acids having 10 to 20 carbon atoms. Examples thereof include oleyl myristate, oleyl stearate, and oleyl oleate; 6) Ether-esters such as fatty acid esters of ethoxylated fatty alcohols; 7) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters; 8) Wax esters such as beeswax, spermaceti, myristyl myristate, stearyl stearate; 9) C1-C30 mono- and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 1:3 molar ratio; and the octaester of sucrose wherein the esterifying carboxylic acid moieties are laurate, linoleate and behenate in a 1:3:4 molar ratio. A suitable solid material is sucrose polyester in which the degree of esterification is 7-8, and in which the fatty acid moieties are C18 mono- and/or di-unsaturated and behenic, in a molar ratio of unsaturates:behenic of 1:7 to 3:5. A particularly suitable solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Amounts of the skin conditioning agent may range from 0% to 30%, from 1% to 20%, or even from 1% to 10% by weight based on the weight of the cosmetic composition.

Solidifying Agent

The present cosmetic compositions can contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition which has a stable physical structure and is deposited on the skin during normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 0 to about 90%, more preferably from about 1 to about 50%, even more preferably from about 5% to about 40%, most preferably from about 1% to about 15%.

Suitable solidifying agents include waxy materials such as candelilla, carnauba waxes, beeswax, spermaceti, carnauba, baysberry, montan, ozokerite, ceresin, paraffin, synthetic waxes such as Fisher-Tropsch waxes, silicone waxes (e.g., DC 2503 from Dow Corning), microcrystalline waxes and the like; soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; and mixtures thereof. Also useful are polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, hydroxypropyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminium silicates, such as, for example, bentonites, or a mixture of polyethylene glycol and polyethylene glycol stearate or distearate. Naturally occurring polymers or biopolymers and their use are further described in European Application No. 522624, to Dunphy et al. Additional examples of naturally occurring polymers or biopolymers can be found in the Cosmetic Bench Reference, pp. 1.40-1.42.

Also useful herein are hydrophilic gelling agents such as the acrylic acid/ethyl acrylate copolymers and the carboxyvinyl polymers sold by the B.F. Goodrich Company under the trademark of Carbopol Registered TM resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name Carbopol Ultrez 10, Carbopol ETD2020, Carbopol 1382, Carbopol 1342 and Pemulen TR-1 (CTFA Designation: Acrylates/10-30 Alkyl Acrylate Crosspolymer). Combinations of the above polymers are also useful herein. Other gelling agents suitable for use herein include oleogels such as trihydroxystearin.

Hydrophobically modified celluloses are also suitable for use herein. These celluloses are described in detail in U.S. Pat. Nos. 4,228,277 and 5,104,646. Additional examples of suitable gelling agents or gellants can be found in the Cosmetic Bench Reference, p. 1.27. Further examples of suitable solidifying agents disclosed in the following references: U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued Jul. 28, 1981; "The Chemistry and Technology of Waxes", A. H. Warth, 2nd Edition, reprinted in 1960, Reinhold Publishing Corporation, pp 391-393 and 421; "The Petroleum Chemicals Industry", R. F. Goldstein and A. L. Waddeam, 3rd Edition (1967), E & F. N. Span Ltd., pp 33-40; "The Chemistry and Manufacture of Cosmetics", M. G. DeNavarre, 2nd edition (1970), Van Nostrand & Company, pp 354-376; and in "Encylopedia of Chemical Technology, Vol. 24, Kirk-Othmer, 3rd Edition (1979) pp 466-481; U.S. Pat. No. 4,126,679, Davy, et al., issued Nov. 21, 1978; European Patent Specification No. 117,070, May, published Aug. 29, 1984; U.S. Pat. No. 2,900, 306, Slater, issued Aug. 18, 1959; U.S. Pat. No. 3,255,082, Barton, issued Jun. 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al., published May 2, 1984; European Patent Specification No. 24,365 Sampson, et al., published Mar. 4, 1981; and U.S. patent application Ser. No. 630,790, DiPietro, filed Jul. 13, 1984.

Preservatives

Suitable traditional preservatives include alkyl esters of para-hydroxybenzoic acid. Other preservatives which have more recently come into use include hydantoin derivatives such as 1,3-bis(hydroxymethyl)-5,5-dimthylhydantoin, propionate salts, and a variety of quaternary ammonium compounds such as benzalkonium chloride, quaternium 15 (Dowicil 200), benzethonium Chloride, and methylbenzethonium chloride. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, sodium benzoate, imidazolidinyl urea (commercially available as Germall 1157), sodium dehydroacetate, capryl hydroxamic acid, caprylyl glycol, methyl propanediol, benzyl alcohol and mixtures of the prior disclosed (such as the Spectrastat series from Inolex). The preservatives should be selected having regard for the use of the composition and possible incompatibilities between the preservatives and other ingredients in the emulsion. Preservatives preferably are employed in amounts ranging from about 0% to about 5%, more preferably from about 0.01% to about 2.5%, and most preferably from about 0.01% to about 1%, by weight of the composition.

Other Optional Ingredients

A variety of additional ingredients can be incorporated into the present cosmetic composition. Nonlimiting examples of these additional ingredients include additional skin care actives such as peptides (e.g., Matrixyl [pentapetide derivative]), farnesol, bisabolol, phytantriol, glycerol, urea, guanidine (e.g., amino guanidine); vitamins and derivatives thereof such ascorbic acid, vitamin A (e.g., retinoid derivatives such as retinyl palmitate or retinyl proprionate), vitamin E (e.g., tocopherol acetate), vitamin $B_3$ (e.g., niacinamide) and vitamin $B_5$ (e.g., panthenol) and the like and mixtures thereof; sunscreens; anti-acne medicaments (resorcinol, salicylic acid, and the like; antioxidants (e.g., phytosterols, lipoic acid); flavonoids (e.g., isoflavones, phytoestrogens); skin soothing and healing agents such as aloe vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol). Nonlimiting examples of suitable carboxylic copolymers, emulsifiers, emollients, and other additional ingredients are disclosed in U.S. Pat. No. 5,011,681, to Ciotti et al., issued Apr. 30, 1991 and U.S. Pat. No. 5,939,082, to Oblong et al., issued Aug. 17, 1999. The above mentioned vitamin $B_3$ compounds can be incorporated as re-crystallized crystals which remain in crystallized form in the composition or as partially solubilize crystals (i.e., some of the crystals are dissolved and some remain in crystalline form in the composition).

Examples

Table 1 shows exemplary embodiments of the present cosmetic composition.

TABLE 1

| - | INCI Name | A | B | C | D | E | F | G | H |
|---|---|---|---|---|---|---|---|---|---|
| DEIONISED WATER | Aqua | 30.580 | 27.870 | 27.870 | 27.870 | 29.000 | 27.870 | 29.300 | 27.870 |
| SODIUM CHLORIDE | Sodium Chloride | 2.000 | 2.000 | 2.000 | 2.000 | 1.500 | 2.000 | 2.250 | 2.000 |
| DC 245 | Cyclopentasiloxane | qs | qs | qs | qs | qs | 0.000 | qs | qs |
| Permethyl 99A | Isododecane | 0.000 | 0.000 | 0.000 | 0.000 | 0.000 | qs | 0.000 | 0.000 |
| PROPYLENE GLYCOL | Propylene Glycol | 8.000 | 6.000 | 6.000 | 4.000 | 10.000 | 6.000 | 6.500 | 6.000 |
| LUVISKOL K17 | PolyVinyl Pyrrolidone | 0.500 | 2.000 | 1.300 | 1.300 | 1.500 | 1.300 | 1.000 | 1.300 |
| THIXCIN R | Trihydroxystearin | 0.350 | 0.265 | 0.265 | 0.265 | 0.250 | 0.265 | 0.300 | 0.265 |
| LAURETH 7 | Laureth-7 | 0.400 | 0.100 | 0.100 | 0.100 | 0.000 | 0.100 | 0.200 | 0.100 |
| DC 5225C | Cyclopentasiloxane and PEG/PPG-18/18 Dimethicone | 21.000 | 21.000 | 21.000 | 21.000 | 20.550 | 21.000 | 20.880 | 21.000 |
| ABIL WE09 | Polyglyceryl 4 Isostearate, Cetyl PEG/PPG-10/1 Dimethicone, Hexyl Laurate | 0.180 | 0.150 | 0.150 | 0.150 | 0.200 | 0.150 | 0.250 | 0.150 |
| MT 100 T | Nano Titanium Dioxide, Aluminium Hydroxide, Stearic Acid | 0.000 | 0.500 | 0.000 | 0.000 | 0.000 | 0.000 | 0.000 | 0.500 |
| SAT-T-CR837 | Titanium Dioxide, Methicone | 8.000 | 2.500 | 9.000 | 8.500 | 7.500 | 8.500 | 4.000 | 8.500 |
| SPHERON P 1500 | Silica | 0.150 | 0.080 | 0.080 | 0.080 | 0.000 | 0.080 | 0.000 | 0.080 |
| HYDROPHOBIC TALC | Talc, Methicone | 0.820 | 1.310 | 0.765 | 0.765 | 1.200 | 0.765 | 2.890 | 0.765 |
| WAXENOL822 | Arachidyl Behenate | 0.250 | 0.300 | 0.300 | 0.300 | 0.100 | 0.300 | 0.150 | 0.300 |
| WAX PT -0602 | Paraffin | 0.150 | 0.150 | 0.150 | 0.150 | 0.200 | 0.150 | 0.200 | 0.150 |
| METHYL PARABEN | Methyl Paraben | 0.120 | 0.000 | 0.000 | 0.000 | 0.000 | 0.000 | 0.000 | 0.000 |
| PROPYL PARABEN | Propyl Paraben | 0.175 | 0.000 | 0.000 | 0.000 | 0.000 | 0.000 | 0.000 | 0.000 |
| SPCAT-12 | Talc & Ethylene/MethacrylateCopolymer & Isopropyl TitaniumTriisostearate | 3.000 | 2.000 | 1.800 | 1.800 | 1.850 | 1.800 | 0.000 | 1.800 |
| Tospearl 145A | Methylsilsequioxane Resin | 0.000 | 0.000 | 0.000 | 0.000 | 0.000 | 0.000 | 2.000 | 0.000 |
| Nylon 12 | Nylon 12 | 0.000 | 0.400 | 0.000 | 0.000 | 0.000 | 0.000 | 0.200 | 0.000 |
| DRY FLO PLUS | Aluminum Starch Octenylsuccinate | 1.250 | 1.000 | 2.250 | 2.250 | 0.000 | 2.250 | 0.100 | 2.250 |
| DC 200 FLUID 350 cs | Dimethicone | 0.000 | 1.000 | 2.400 | 2.400 | 1.000 | 2.400 | 2.400 | 0.000 |
| DC 200 50 cs | Dimethicone | 2.250 | 4.200 | 0.000 | 0.000 | 4.200 | 0.000 | 0.000 | 0.000 |
| DC 200 50 cs | Dimethicone | 0.000 | 0.000 | 0.000 | 0.000 | 0.000 | 5.000 | 0.000 | 0.000 |
| TRIETHANOLAMINE | Triethanolamine | 2.000 | 0.000 | 0.000 | 0.000 | 0.000 | 0.000 | 0.000 | 0.000 |
| PBSA | Phenylbenzimidazole Sulphonic Acid | 2.750 | 2.750 | 3.000 | 3.000 | 1.500 | 3.000 | 2.750 | 0.500 |
| OMC | OctylMethoxy Cinnamate | 0.000 | 0.000 | 0.000 | 0.000 | 0.000 | 0.000 | 0.000 | 3.000 |
| CM3FA65EBH (black) | Cyclopentasiloxane & iron Oxides (C.I.77499) & PEG/ppg-18/18 Dimethicone & Methicone | 0.220 | 0.310 | 0.220 | 0.220 | 0.220 | 0.220 | 0.220 | 0.220 |
| CM3FA70ERH (red) | Cyclopentasiloxane & iron Oxides (C.I.77491) & PEG/ppg-18/18 Dimethicone & Methicone | 0.740 | 0.120 | 0.740 | 0.740 | 0.740 | 0.740 | 0.740 | 0.740 |
| CM3FA55EYH (yellow) | Cyclopentasiloxane & iron Oxides (C.I.77492) & PEG/ppg-18/18 Dimethicone & Methicone | 3.860 | 0.000 | 3.860 | 3.860 | 3.860 | 3.860 | 3.860 | 3.860 |
| FX50-DMC4 | Iron Containing Titanium Dioxide | 0.000 | 4.500 | 0.000 | 0.000 | 0.000 | 0.000 | 0.000 | 0.000 |
| FAF40TRR | Transparent Red Iron Oxide | 0.000 | 1.200 | 0.000 | 0.000 | 0.000 | 0.000 | 0.000 | 0.000 |
| FAF40TRY | Transparent Yellow Iron Oxide | 0.000 | 0.100 | 0.000 | 0.000 | 0.000 | 0.000 | 0.000 | 0.000 |

TABLE 1-continued

| | INCI Name | A | B | C | D | E | F | G | H |
|---|---|---|---|---|---|---|---|---|---|
| ETHYLENE BRASSYLATE | Ethylene Brassylate | 0.050 | 0.050 | 0.050 | 0.000 | 0.000 | 0.050 | 0.050 | 0.050 |
| PERFUME ENTRAPPED IN SOLID PARTICLES | | 0.000 | 0.000 | 0.000 | 1.034 | 0.000 | 0.000 | 0.000 | 0.000 |
| 10% SODIUM HYDROXIDE SOLUTION | Sodium Hydroxide, Water | 0.000 | 3.750 | 3.750 | 3.750 | 4.100 | 3.750 | 3.750 | 1.000 |
| PHENOXYETHANOL | Phenoxyethanol | 0.000 | 0.480 | 0.480 | 0.480 | 0.500 | 0.420 | 0.375 | 0.480 |
| SODIUM BENZOATE | Sodium Benzoate | 0.000 | 0.150 | 0.150 | 0.150 | 0.100 | 0.150 | 0.075 | 0.150 |
| BENZYL ALCOHOL | Benzyl Alcohol | 0.000 | 0.450 | 0.450 | 0.450 | 0.300 | 0.450 | 0.300 | 0.450 |
| SILICA SHELLS SH | Silica & Methoxy Amodimethicone/Silsesquioxane Copolymer | 0.000 | 0.000 | 0.000 | 0.000 | 0.000 | 0.000 | 1.250 | 0.000 |
| TOTAL | | 100 | 100 | 100 | 100 | 100 | 100 | 100 | 100 |

TABLE 2

| | Sample | |
|---|---|---|
| | A | B |
| # of Respondents | 59 | 69 |
| Questions | | |
| Shade Not Chg/Fade Thru Day | 82 | 75 |
| No Shine Brkthru Thru Day | 75 | 67 |
| Keeps Matte Look Thru Day | 75 | 67 |
| Not Rub Off Thru Day | 76 | 71 |
| Matte Finish Upon Application | 85 | 73 |
| Feels Smooth Dur Application | 84 | 78 |
| Skin Not Feel Greasy/Oily | 82 | 68 |

Table 2 illustrates the results of a comparative test to distinguish an embodiment of the present cosmetic composition from a commercially available cosmetic composition. Sample A is an exemplary embodiment of the present cosmetic composition in the form of a foundation. Sample B is L'Oreal® Infallible® brand foundation, which is available from L'Oreal Societe Anonyme, Paris, France. As can be seen in Table 2, the cosmetic composition herein provides a long-wear, matte-appearance benefit relative to the comparative product. To administer the test, 59 panelists are selected and asked the questions shown in the rows underneath "Questions" with regard to the present composition. An additional 69 panelists are selected and asked the same questions with regard to the comparative product. The panelists were selected based on their acceptance of the shade of the test products. Depending on the product being tested and the variation in shades, shade acceptance can cause the base sizes of different products to vary somewhat.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin cosmetic in the form of a foundation composition, comprising:

an aqueous phase that includes from 0.5% to 10% by weight based on the weight of the composition of film-forming polyvinylpyrrolidone polymer that adheres to skin when the composition is applied to the skin;

0.1%-16% by weight based on the weight of the composition of a sunscreen active selected from the group consisting of titanium dioxide, zinc oxide, 2-ethylhexyl-p-methoxycinnamate, 4-isopropyldibenzoylmethane, 4-(1,1-dimethylethyl)-4'-methoxydibenzoylmethane, 2-ethylhexyl-2-cyano-3,3-diphenylacrylate, 2-phenylbenzimidaole-5-sulfonic acid;

0.01%-40% by weight based on the weight of the composition of a multitude of particles comprising a mixture of Surface Topography Modifier particles, Locking Oil Absorber particles, and Releasing Oil Absorber particles wherein the multitude of particles are present at a ratio of Surface Topography Modifier:Locking Oil Asorber:Releasing Oil Absorber of from 25:25:1 to 15:5:1; wherein aluminum starch octenylsuccinate having a size in the range of 10 to 75 microns is the Surface Topography Modifier particle, mixture of talc and isopropyl titanium triisostearate and ethylene/methacrylate copolymer microspheres having a particle size of 15-50 microns are the Locking Oil Absorber particles and silica having a particle size of 1-20 microns is the Releasing Oil Absorber particle and said foundation composition optionally further comprising particles selected from the group consisting of hydrated silica, silicone treated silica beads, mica, talc, nylon 12, nylon 6, polyethylene, methyl silsesquioxane resin, polymethylmethacrylate, crosslinked polydimethylsiloxanes, polyamide, polystyrene, polyethylene, Styrene/DVB copolymers, and mixtures thereof from 0.5% to 30% of propylene glycol as the plasticizing solvent, wherein the ratio of propylene glycol to film-forming polyvinyl pyrrolidone is between 10:1 to 1:1 and the foundation composition comprising at least one of an emulsifier, an elastomer, a metal oxide, and a fragrance wherein the metal oxide is included in an amount of from 0.05% to 15% by weight based on the weight of the foundation composition, and the metal oxide is selected from the group consisting of pigmentary grade iron oxide particles, pigmentary grade titanium dioxide particles, and combinations thereof and the elastomer is included in the foundation composition in an amount of from 0.01% to 15% by weight based on the weight of the foundation composition, and the elastomer is a cross-linked organo polysiloxane elastomer; and an oil phase that includes from 1% to 80% by weight based on the weight of the composition of an oil.

2. The cosmetic composition of claim 1, wherein the oil has at least one of a vapor pressure of no more than 0.2 mm Hg at 25° C. and one atmosphere, and a boiling point at one atmosphere of at least 300° C.

3. The cosmetic composition of claim 1, wherein the oil has a solubility parameter of less 6.5 $(cal/cm^3)^{0.5}$.

4. The foundation composition of claim 1, wherein the cross-linked organopolysiloxane elastomer includes at least one polyoxyalkylene or polygyceryl group.

* * * * *